US011833237B2

(12) United States Patent
Wise

(10) Patent No.: US 11,833,237 B2
(45) Date of Patent: Dec. 5, 2023

(54) METHOD FOR ENHANCING SCALP ACTIVE DEPOSITION

(71) Applicant: The Procter & Gamble Company, Cincinnati, OH (US)

(72) Inventor: Geoffrey Marc Wise, Reading, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 212 days.

(21) Appl. No.: 17/196,379

(22) Filed: Mar. 9, 2021

(65) Prior Publication Data
US 2022/0287942 A1 Sep. 15, 2022

(51) Int. Cl.
A61K 8/49 (2006.01)
A61K 8/23 (2006.01)
A61K 8/81 (2006.01)
A61Q 5/02 (2006.01)

(52) U.S. Cl.
CPC .............. A61K 8/4953 (2013.01); A61K 8/23 (2013.01); A61K 8/817 (2013.01); A61K 8/8152 (2013.01); A61Q 5/02 (2013.01); A61K 2800/5424 (2013.01); A61K 2800/5426 (2013.01); A61K 2800/58 (2013.01); A61K 2800/805 (2013.01)

(58) Field of Classification Search
CPC .. A61K 2800/805; A61K 8/042; A61K 8/062; A61K 8/39; A61K 8/891; A61K 2800/41; A61K 8/06; A61K 8/73; A61K 8/731; A61K 8/8152; A61K 47/60; A61K 47/6931; A61K 49/0002; A61K 49/0093; A61K 49/186; A61K 49/1866; A61K 51/1255; A61K 9/5161; A61K 9/5192; A61K 2800/5424; A61K 2800/5426; A61K 2800/58; A61K 8/23; A61K 8/27; A61K 8/4953; A61K 8/817; A61K 2800/33; A61K 8/342; A61K 8/463; A61K 8/494; A61K 8/89; A61Q 5/02; A61Q 5/06; A61Q 5/12
See application file for complete search history.

(56) References Cited

U.S. PATENT DOCUMENTS

| 823,725 | A | 6/1906 | Hayden |
|---|---|---|---|
| 3,293,684 | A | 12/1966 | Otto |
| 3,956,158 | A | 5/1976 | Donaldson |
| 4,107,289 | A | 8/1978 | Kaufman |
| 4,203,857 | A | 5/1980 | Dugan |
| 4,322,400 | A | 3/1982 | Yuhas |
| 4,486,404 | A | 12/1984 | Weinert |
| 4,808,467 | A | 2/1989 | Suskind et al. |
| 5,144,729 | A | 9/1992 | Austin et al. |
| 5,160,739 | A | 11/1992 | Kanga |
| 5,340,492 | A | 8/1994 | Kacher et al. |
| 5,340,571 | A | 8/1994 | Grace |
| 5,425,892 | A | 6/1995 | Taneri et al. |
| 5,436,278 | A | 7/1995 | Imashiro et al. |
| 5,525,397 | A | 6/1996 | Shizuno et al. |
| 5,585,092 | A | 12/1996 | Trandai et al. |
| 5,605,681 | A | 2/1997 | Trandai et al. |
| 5,691,035 | A | 11/1997 | Chappell et al. |
| 5,846,520 | A | 12/1998 | Guskey et al. |
| 5,916,590 | A | 6/1999 | Cody et al. |
| 6,042,815 | A | 3/2000 | Kellner et al. |
| 6,143,393 | A | 11/2000 | Abe et al. |
| 6,241,835 | B1 | 6/2001 | Abe et al. |
| 6,245,413 | B1 | 6/2001 | Kenmochi et al. |
| 6,329,308 | B1 | 12/2001 | Kenmochi et al. |
| 6,550,092 | B1 | 4/2003 | Brown et al. |
| 6,554,937 | B1 | 4/2003 | Kenmochi et al. |
| 6,774,070 | B1 | 8/2004 | Kenmochi et al. |
| 6,777,064 | B1 | 8/2004 | Brown et al. |
| 6,797,357 | B2 | 9/2004 | Fereshtehkhou et al. |
| 6,813,801 | B2 | 11/2004 | Tanaka et al. |
| 6,936,330 | B2 | 8/2005 | Fereshtehkhou et al. |
| 6,974,569 | B2 | 12/2005 | Dunlop et al. |
| 7,003,856 | B2 | 2/2006 | Hayashi et al. |
| 7,026,308 | B1 | 4/2006 | Gavin et al. |
| 7,291,359 | B2 | 11/2007 | Haskett et al. |
| 7,386,907 | B2 | 6/2008 | Otsuka et al. |
| 7,560,398 | B2 | 7/2009 | Zillig et al. |
| 7,566,671 | B2 | 7/2009 | Hoadley et al. |
| 7,712,178 | B2 | 5/2010 | Yamada |
| 7,779,502 | B2 | 8/2010 | Fujiwara et al. |
| 7,937,797 | B2 | 5/2011 | Tsuchiya et al. |
| 8,075,977 | B2 | 12/2011 | Curro et al. |

(Continued)

FOREIGN PATENT DOCUMENTS

| CA | 680113 A | 2/1964 |
|---|---|---|
| CN | 107440935 A | 12/2017 |

(Continued)

OTHER PUBLICATIONS

15995 PCT Search Report and Written Opinion for PCT/US2022/019234 dated Jul. 21, 2022, 13 pages.
All Office Actions; U.S. Appl. No. 17/225,146, filed Apr. 8, 2021.
All Office Actions; U.S. Appl. No. 17/225,147, filed Apr. 8, 2021.
All Office Actions; U.S. Appl. No. 17/225,148, filed Apr. 8, 2021.
All Office Actions; U.S. Appl. No. 17/225,149, filed Apr. 8, 2021.
All Office Actions; U.S. Appl. No. 17/225,150, filed Apr. 8, 2021.
All Office Actions; U.S. Appl. No. 17/225,151, filed Apr. 8, 2021.
All Office Actions; U.S. Appl. No. 17/225,153, filed Apr. 8, 2021.
All Office Actions; U.S. Appl. No. 17/225,176, filed Apr. 8, 2021.
All Office Actions; U.S. Appl. No. 17/225,218, filed Apr. 8, 2021.

(Continued)

Primary Examiner — Audrea B Coniglio
(74) Attorney, Agent, or Firm — Linda M. Sivik

(57) ABSTRACT

The present invention is directed to a method of making a personal care composition comprising the following steps: combine a particulate scalp active with an anionic polymer to form a mixture (a); combine the mixture (a) with a cationic polymer having a charge density of 3 to 10 meq/gram to form a mixture (b); combine mixture (b) into a personal care composition base.

19 Claims, No Drawings

(56) References Cited

U.S. PATENT DOCUMENTS

| | | | |
|---|---|---|---|
| 8,093,192 B2 | 1/2012 | Liu et al. | |
| 8,146,197 B2 | 4/2012 | Yamada | |
| 8,151,402 B2 | 4/2012 | Takabayashi et al. | |
| 8,161,594 B2 | 4/2012 | Policicchio et al. | |
| 8,186,001 B2 | 5/2012 | Tsuchiya et al. | |
| 8,225,453 B2 | 7/2012 | Yamada | |
| 8,245,349 B2 | 8/2012 | Tsuchiya et al. | |
| 8,435,625 B2 | 5/2013 | Ruehe et al. | |
| 8,528,151 B2 | 9/2013 | Przepasniak | |
| 8,536,074 B2 | 9/2013 | Fereshtehkhou et al. | |
| 8,617,685 B2 | 12/2013 | Yamada | |
| 8,646,144 B2 | 2/2014 | Wada et al. | |
| 8,752,232 B2 | 6/2014 | Otsuka et al. | |
| 8,756,746 B2 | 6/2014 | Policicchio | |
| 8,763,197 B2 | 7/2014 | Policicchio et al. | |
| 8,793,832 B2 | 8/2014 | Yamada | |
| 8,851,776 B2 | 10/2014 | Schwarz et al. | |
| 8,858,971 B2 | 10/2014 | Rao | |
| 9,113,768 B2 | 8/2015 | Wada et al. | |
| 9,198,553 B2 | 12/2015 | Policicchio | |
| 9,204,775 B2 | 12/2015 | Pung et al. | |
| 9,296,176 B2 | 3/2016 | Escaffre et al. | |
| 9,339,165 B2 | 5/2016 | Vetter et al. | |
| 9,622,943 B2 | 4/2017 | Scala et al. | |
| 10,076,583 B2 | 9/2018 | Lynch | |
| 10,143,632 B2 | 12/2018 | Dihora et al. | |
| 10,143,764 B2 | 12/2018 | Lynch | |
| 10,821,056 B2 | 11/2020 | Swartz et al. | |
| 10,835,455 B2 | 11/2020 | Payne et al. | |
| 10,932,996 B2 | 3/2021 | Baig et al. | |
| 2001/0048933 A1 | 12/2001 | L Alloret | |
| 2002/0160088 A1 | 10/2002 | Sakaguchi et al. | |
| 2003/0021760 A1 | 1/2003 | Kumar et al. | |
| 2003/0053980 A1 | 3/2003 | Dodd et al. | |
| 2004/0185011 A1 | 9/2004 | Alexander | |
| 2005/0152851 A1 | 7/2005 | Kaminski | |
| 2006/0024245 A1 | 2/2006 | Gebreselassie et al. | |
| 2009/0155190 A1 | 6/2009 | Gebreselassie et al. | |
| 2011/0027328 A1 | 2/2011 | Baig et al. | |
| 2011/0053826 A1* | 3/2011 | Wise | C11D 11/0094 510/495 |
| 2011/0262507 A1 | 10/2011 | Spring | |
| 2011/0305739 A1 | 12/2011 | Royce | |
| 2013/0111682 A1 | 5/2013 | Pung | |
| 2013/0302385 A1 | 11/2013 | Muenz et al. | |
| 2014/0289984 A1 | 10/2014 | Vetter | |
| 2015/0196185 A1 | 7/2015 | Fiske | |
| 2015/0216774 A1 | 8/2015 | Yu et al. | |
| 2015/0313803 A1 | 11/2015 | Lynch et al. | |
| 2015/0313808 A1 | 11/2015 | Lynch et al. | |
| 2015/0368443 A1 | 12/2015 | Rincon et al. | |
| 2016/0120771 A1 | 5/2016 | Simonet et al. | |
| 2016/0346175 A1* | 12/2016 | Sasik | A61K 8/891 |
| 2017/0151157 A1 | 6/2017 | Gevgilili et al. | |
| 2018/0028433 A1 | 2/2018 | Punsch et al. | |
| 2018/0127692 A1 | 5/2018 | Coope-Epstein et al. | |
| 2019/0062173 A1 | 2/2019 | Wise | |
| 2019/0160022 A1 | 5/2019 | Chiou | |
| 2019/0298625 A1 | 10/2019 | Hilliard, Jr. et al. | |
| 2019/0343732 A1 | 11/2019 | Mao | |
| 2020/0000693 A1 | 1/2020 | Traynor et al. | |
| 2021/0007940 A1 | 1/2021 | Swartz et al. | |
| 2021/0315434 A1 | 10/2021 | Lynch et al. | |
| 2021/0315435 A1 | 10/2021 | Lynch et al. | |
| 2021/0315783 A1 | 10/2021 | Lynch et al. | |
| 2021/0315784 A1 | 10/2021 | Lynch et al. | |
| 2021/0315812 A1 | 10/2021 | Lynch et al. | |
| 2021/0322287 A1 | 10/2021 | Lynch et al. | |
| 2021/0322290 A1 | 10/2021 | Lynch et al. | |
| 2021/0322322 A1 | 10/2021 | Lynch et al. | |
| 2021/0330565 A1 | 10/2021 | Lynch et al. | |
| 2022/0010245 A1 | 1/2022 | Lynch et al. | |

FOREIGN PATENT DOCUMENTS

| | | | |
|---|---|---|---|
| DE | 202007001353 U1 | 5/2007 | |
| EP | 0916722 A2 | 5/1999 | |
| EP | 2465487 A2 | 6/2012 | |
| EP | 2170257 B1 | 11/2012 | |
| GB | 2221389 A | 2/1990 | |
| WO | 9209679 A1 | 6/1992 | |
| WO | 9966886 A1 | 12/1999 | |
| WO | 03075735 A1 | 9/2003 | |
| WO | 2009095891 A1 | 8/2009 | |
| WO | 2010060653 A2 | 6/2010 | |
| WO | WO2014/124066 A1 * | 8/2014 | A61Q 5/12 |

OTHER PUBLICATIONS

All Office Actions; U.S. Appl. No. 17/485,906, filed Sep. 27, 2021.

Clinton D. Stevenson, et al., "Capillary Pressure as Related to Water Holding in Polyacrylamide and Chicken Protein Gels", Journal of Food Science, vol. 78, Nr. 2, dated 2013,pp. C145-C151.

F. V. Ryer, Oil & Soap, "Research Laboratory, Lever Brothers Company Cambridge, Massachusetts", dated Oct. 1946, pp. 310-313.

F. V. Ryer, et al. Growing Single Crystals, "A Method of Growing Single Crystals Of Sodium Stearate And Sodium Palmitate", dated Feb. 4, 1944, pp. 154-158.

Marc N. G. de Mul, et al. Langmuir 2000, "Solution Phase Behavior and Solid Phase Structure of Long-Chain Sodium Soap Mixtures", vol. 16, No. 22, dated 2000, pp. 8276-8284.

Masao Sambuichi, et al. Dewatering Of Gels, "Filtration, Food Chemical Engineering, Solid Liquid Separation, Dewatering, Expression, Gel", Journal of Chemical Engineering of Japan, vol. 27, No. 5, dated 1994, pp. 616-620.

Matthew L Lynch, Acid-soaps, "The study of acid-soap crystals has resulted in many conflicting data", Current Opinion in Colloid & Interface Science, dated 1997,pp. 495-500.

Matthew L. Lynch, et al. Acid-soap crystals, "Spectroscopic and Thermal Characterization of 1:2 Sodium Soap/Fatty Acid Acid-Soap Crystals", J. Phys. Chem., vol. 100, No. 1, 1996, pp. 357-361.

Matthew L. Lynch, Structure of Fatty Acid-Soap Crystals,"Intermolecular Interactions and the Structure of Fatty Acid-Soap Crystals", J. Phys. Chem. B, vol. 105, No. 2, dated 2001, pp. 552-561.

Theodore P. Labuza, et al., "Measurement Of Gel Water-Binding Capacity By Capillary Suction Potential", Journal of Food Science, vol. 43, dated 1978 ,pp. 1264-1269.

* cited by examiner

METHOD FOR ENHANCING SCALP ACTIVE DEPOSITION

FIELD OF THE INVENTION

The present invention is directed to a method for enhancing scalp active deposition and providing a stable, efficacious personal care composition with no tradeoffs in cosmetic conditioning performance.

BACKGROUND OF THE INVENTION

Hydrophobic anti-dandruff actives have poor deposition efficiency on hair and body. Coacervation (from low-charge-density polymers that are soluble in the product) can aid deposition, but when used at the high levels needed for effective deposition, they can hinder bioavailability of the actives. Moreover, the deposition performance of these coacervating systems is sensitive to changes in the personal care base composition, such as the type and level of surfactants and electrolytes, necessitating continuous experimentation when changing the base formulation, with uncertain impact on the consumer acceptance and stability of the formula. There can also be competition between deposition of conditioning actives and anti-dandruff actives, particularly when these active have particle which differ in size. A solution is needed to drive effective anti-dandruff deposition independent of coacervation, such that anti-dandruff actives can be deployed easily across a broad range of formulas to meet ever-changing consumer desires for cosmetically pleasing anti-dandruff shampoos that are also effective and stable

SUMMARY OF THE INVENTION

The present invention is directed to a method of making a personal care composition comprising the following steps: combine a particulate scalp active with an anionic polymer to form a mixture (a); combine the mixture (a) with a cationic polymer having a charge density of 3 to 10 meq/gram to form a mixture (b); combine mixture (b) into a personal care composition base.

DETAILED DESCRIPTION OF THE INVENTION

While the specification concludes with claims which particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

The term "coacervate" as used herein, means the complex which forms between surfactant and polymer, either in the neat composition or upon dilution during consumer use.

"Personal Care Composition Base" as used herein may comprise one or more detersive surfactants, aqueous carriers and other additional components of the personal care composition. Minor ingredients such as anti-dandruff actives, fragrance, conditioning oils can be included in the base or added later to the base for ease of creating different compositions with a common core set of ingredients.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free" of as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

Scalp Active

The present invention may comprise a scalp active, which may be a particulate scalp active and further may be an anti-dandruff active. Further, the particulate scalp active may be a particulate anti-dandruff actives and this group may include pyridinethione salts; zinc carbonate; selenium sulphide; particulate sulfur; strobilurins such as azoxystrobin; and mixtures thereof. The scalp active particulate /anti-dandruff particulate may be a pyridinethione salt. Such anti-dandruff particulate should be physically and chemically compatible with the components of the composition, and should not otherwise unduly impair product stability, aesthetics or performance The concentration of the scalp active may be in the range of from about 0.1% to about 10%; from about 0.25% to about 5%; from about 0.25% to about 4%; from about 2% to about 4%; from about 1% to about 2%.

Pyridinethione particulates are suitable particulate anti-dandruff actives for use in composition of the present invention. The anti-dandruff active may be a 1-hydroxy-2-pyridinethione salt and is in particulate form. The concentration of pyridinethione anti-dandruff particulate may range from about 0.01% to about 5%, by weight of the composition, or from about 0.1% to about 3%, or from about 1% to about 2%. The pyridinethione salts may be those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. The 1-hydroxy-2-pyridinethione salts may be in platelet particle form having an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753, 196; 3,761,418; 4,345,080; 4,323,683; 4,379,753; and 4,470,982.

In addition to the particulate anti-dandruff active above, the composition may further comprise one or more anti-fungal and/or anti-microbial actives. The anti-microbial active may be selected from the group consisting of: coal tar, sulfur, charcoal, copper pyrithione, whitfield's ointment, castellani's paint, aluminium chloride, gentian violet, hydroxyl pyridine and wherein the hydroxyl pyridine may be piroctone olamine, octopirox (piroctone olamine), ciclopirox olamine, rilopirox, MEA-Hydroxyoctyloxypyridinone; and metal chelators such as 1,10-phenanthroline, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. The anti-microbial may be selected from the group consisting of: itraconazole, ketoconazole, selenium sulphide, coal tar, and mixtures thereof.

The azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. The azole anti-microbial active may be ketoconazole. The sole anti-microbial active may be ketoconazole.

The present invention may also comprise a combination of anti-microbial actives. The combination of anti-microbial active may be selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

The composition may comprise an effective amount of a zinc-containing layered material. The composition may comprise from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM may be a layered double hydroxide conforming to the formula $[M^{2+}_{1-x}M^{3+}_x(OH)_2]^{x+} A^{m-}_{x/m} \cdot nH_2O$ wherein some or all of the divalent ions ($M^{2+}$) are zinc ions (Crepaldi, EL, Pava, PC, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). The ZLM may be a hydroxy double salt conforming to the formula $[M^{2+}_{1-x}M^{2+}_{1+x}(OH)_{3(1-y)}]^{+} A^{n-}_{(1=3y)/n} \cdot nH_2O$ where the two metal ions ($M^2\pm$) may be the same or different. If they are the same and represented by zinc, the formula simplifies to $[Zn_{1+x}(OH)_2]^{2x+} 2x\ A^- \cdot nH_2O$. This latter formula represents (where x=0.4) materials such as zinc hydroxychloride and zinc hydroxynitrate. THe ZLM may be zinc hydroxychloride and/or zinc hydroxynitrate. These are related to hydrozincite as well wherein a divalent anion replace the monovalent anion. These materials can also be formed in situ in a composition or in or during a production process.

The composition may comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

The composition may contain a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Detersive Surfactant

The personal care composition may comprise greater than about 10% by weight of a surfactant system which provides cleaning performance to the composition, and may be greater than 12% by weight of a surfactant system which provides cleaning performance to the composition. The surfactant system comprises an anionic surfactant and/or a combination of anionic surfactants and/or a combination of anionic surfactants and co-surfactants selected from the group consisting of amphoteric, zwitterionic, nonionic and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

The personal care composition may comprise from about 10% to about 25%, from about 10% to about 18%, from about 10% to about 14%, from about 10% to about 12%, from about 11% to about 20%, from about 12% to about 20%, and/or from about 12% to about 18% by weight of one or more surfactants.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the personal care composition include ammonium lauryl sulfate, ammonium laureth sulfate, ammonium C10-15 pareth sulfate, ammonium C10-15 alkyl sulfate, ammonium C11-15 alkyl sulfate, ammonium decyl sulfate, ammonium deceth sulfate, ammonium undecyl sulfate, ammonium undeceth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium C10-15 pareth sulfate, sodium C10-15 alkyl sulfate, sodium C11-15 alkyl sulfate, sodium decyl sulfate, sodium deceth sulfate, sodium undecyl sulfate, sodium undeceth sulfate, potassium lauryl sulfate, potassium laureth sulfate, potassium C10-15 pareth sulfate, potassium C10-15 alkyl sulfate, potassium C11-15 alkyl sulfate, potassium decyl sulfate, potassium deceth sulfate, potassium undecyl sulfate, potassium undeceth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

The composition of the present invention can also include anionic surfactants selected from the group consisting of:
a) $R_1\ O(CH_2CHR_{30})_y SO_3M$;
b) $CH_3\ (CH_2)_z\ CHR_2\ CH_2\ O\ (CH_2\ CHR_3O)_y\ SO_3M$; and
c) mixtures thereof, where $R_1$ represents $CH_3\ (CH_2)_{10}$, R2 represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

Suitable anionic alkyl sulfates and alkyl ether sulfate surfactants include, but are not limited to, those having branched alkyl chains which are synthesized from C8 to C18 branched alcohols which may be selected from the group consisting of: Guerbet alcohols, aldol condensation derived alcohols, oxo alcohols, F-T oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol , 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISO- FOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfate and sodium trideceth-3 sulfate. The composition of the present invention can also include sodium tridecyl sulfate.

The composition of the present invention can also include anionic alkyl and alkyl ether sulfosuccinates and/or dialkyl and dialkyl ether sulfosuccinates and mixtures thereof. The dialkyl and dialkyl ether sulfosuccinates may be a C6-15 linear or branched dialkyl or dialkyl ether sulfosuccinate. The alkyl moieties may be symmetrical (i.e., the same alkyl moieties) or asymmetrical (i.e., different alkyl moieties). Nonlimiting examples include: disodium lauryl sulfosuccinate, disodium laureth sulfosuccinate, sodium bistridecyl sulfosuccinate, sodium dioctyl sulfosuccinate, sodium dihexyl sulfosuccinate, sodium dicyclohexyl sulfosuccinate, sodium diamyl sulfosuccinate, sodium diisobutyl sulfosuccinate, linear bis(tridecyl) sulfosuccinate and mixtures thereof.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

"Substantially free" of sulfate based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

The personal care composition may comprise a co-surfactant. The co-surfactant can be selected from the group consisting of amphoteric surfactant, zwitterionic surfactant, non-ionic surfactant and mixtures thereof. The co-surfactant can include, but is not limited to, lauramidopropyl betaine, cocoamidopropyl betaine, lauryl hydroxysultaine, sodium lauroamphoacetate, disodium cocoamphodiacetate, cocamide monoethanolamide and mixtures thereof.

The personal care composition may further comprise from about 0.25% to about 15%, from about 1% to about 14%, from about 2% to about 13% by weight of one or more amphoteric, zwitterionic, nonionic co-surfactants, or a mixture thereof.

Suitable amphoteric or zwitterionic surfactants for use in the personal care composition herein include those which are known for use in shampoo or other personal care cleansing. Non limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, thoseselected from the group consisting of: sodium cocaminopropionate, sodium cocaminodipropionate, sodium cocoamphoacetate, sodium cocoamphodiacetate, sodium cocoamphohydroxypropylsulfonate, sodium cocoamphopropionate, sodium cornamphopropionate, sodium lauraminopropionate, sodium lauroamphoacetate, sodium lauroamphodiacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphodiacetate, ammonium cocoamphohydroxypropylsulfonate, ammonium cocoamphopropionate, ammonium cornamphopropionate, ammonium lauraminopropionate, ammonium lauroamphoacetate, ammonium lauroamphodiacetate, ammonium lauroamphohydroxypropylsulfonate, ammonium lauroamphopropionate, ammonium cornamphopropionate, ammonium lauriminodipropionate, triethanolamine cocaminopropionate, triethanolamine cocaminodipropionate, triethanolamine cocoamphoacetate, triethanolamine cocoamphohydroxypropylsulfonate, triethanolamine cocoamphopropionate, triethanolamine cornamphopropionate, triethanolamine lauraminopropionate, triethanolamine lauroamphoacetate, triethanolamine lauroamphohydroxypropylsulfonate, triethanolamine lauroamphopropionate, triethanolamine cornamphopropionate, triethanolamine lauriminodipropionate, cocoamphodipropionic acid, disodium caproamphodiacetate, disodium caproamphoadipropionate, disodium capryloamphodiacetate, disodium capryloamphodipriopionate, disodium cocoamphoc arboxyethylhydroxypropylsulfonate, di sodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The composition may comprises a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof.

Suitable nonionic surfactants for use in the present invention include those described in McCutcheion's Detergents and Emulsifiers, North American edition (1986), Allured Publishing Corp., and McCutcheion's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

The co-surfactant can be a non-ionic surfactant selected from the alkanolamides group including: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, PPG-2 Hydroxyethyl Isostearamide and mixtures thereof.

Representative polyoxyethylenated alcohols include alkyl chains ranging in the C9-C16 range and having from about 1 to about 110 alkoxy groups including, but not limited to, laureth-3, laureth-23, ceteth-10, steareth-10, steareth-100, beheneth-10, and commercially available from Shell Chemicals, Houston, Tex. under the trade names Neodol® 91, Neodol® 23, Neodol® 25, Neodol® 45, Neodol® 135, Neodo®1 67, Neodol® PC 100, Neodol® PC 200, Neodol® PC 600, and mixtures thereof.

Also available commercially are the polyoxyethylene fatty ethers available commercially under the Brij® trade name from Uniqema, Wilmington, Delaware, including, but not limited to, Brij® 30, Brij® 35, Brij® 52, Brij® 56, Brij® 58, Brij® 72, Brij® 76, Brij® 78, Brij® 93, Brij® 97, Brij® 98, Brij® 721 and mixtures thereof.

Suitable alkyl glycosides and alkyl polyglucosides can be represented by the formula (S)n-O-R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein S is a glucose moiety, R is a C8-20 alkyl group, and n is an integer of from about 1 to about 9. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names Triton™ BG-10 and Triton™ CG-110 from The Dow Chemical Company, Houston, Tex.

Other nonionic surfactants suitable for use in the present invention are glyceryl esters and polyglyceryl esters, including but not limited to, glyceryl monoesters, glyceryl monoesters of C12-22 saturated, unsaturated and branched chain fatty acids such as glyceryl oleate, glyceryl monostearate, glyceryl monopalmitate, glyceryl monobehenate, and mixtures thereof, and polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof.

Also useful herein as nonionic surfactants are sorbitan esters. Sorbitan esters of C12-22 saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), and mixtures thereof, all available from Uniqema.

Also suitable for use herein are alkylphenol ethoxylates including, but not limited to, nonylphenol ethoxylates (Tergitol™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tex.) and octylphenol ethoxylates (Triton™ X-15, X-35, X-45, X-114, X-100, X-102, X-165, X-305, X-405, X-705 available from The Dow Chemical Company, Houston, Tex.).

Also suitable for use herein are tertiary alkylamine oxides including lauramine oxide and cocamine oxide.

Non limiting examples of other anionic, zwitterionic, amphoteric, and non-ionic additional surfactants suitable for use in the personal care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable surfactant combinations comprise an average weight % of alkyl branching of from about 0.5% to about 30%, alternatively from about 1% to about 25%, alternatively from about 2% to about 20%. The surfactant combination can have a cumulative average weight % of C8 to C12 alkyl chain lengths of from about 7.5% to about 25%, alternatively from about 10% to about 22.5%, alternatively from about 10% to about 20%. The surfactant combination can have an average C8-C12/C13-C18 alkyl chain ratio from about 3 to about 200, alternatively from about 25 to about 175.5, alternatively from about 50 to about 150, alternatively from about 75 to about 125.

Anionic Polymer

The composition of the present invention may further contain an anionic polymer. The anionic polymer can be used at levels by weight of the composition of from about 0.0005% to about 0.5%, from about 0.002% to about 0.30%, from about 0.01% to about 0.2% in view of improving suspension of scalp actives, improving deposition of scalp actives, and/or improving stability of personal care formulations.

The weight ratio of the anionic polymer to scalp active, may be from about 1:1 to about 1:100, from about 1:5 to about 1:50; from about 1:8 to about 1:20, in view of improving suspension of scalp active while maintaining enough available scalp active surface area to ensure bioavailability upon deposition In the present invention the weight ratio of the anionic polymer to cationic polymer, is from about 1000:1 to about 1:35, from about 100:1 to about 1:20 from about 10:1 to about 1:10 in view of achieving efficient polymer-polymer coacervation which would lead to high deposition of actives onto the surface.

Anionic polymers useful herein are, for example, those having a molecular weight of from about 100 g/mol to about 1,000,000 g/mol; from about 1,000 g/mol to about 100,000 g/mol; from about 1,000g/mol to about 10,000g/mol; from about 1,000 g/mol to about 5,000 g/mol in comparison to standards of sodium poly(styrenesulfonate) in view of having the ability to suspend solids and prevent their agglomeration, and those having a charge density of from about 1.0 meq/g to about 10 meq/g; from about 2.0 meq/g to about 7 meq/g; from about 3.0 meq/g to about 5.0 meq/g in view of compatibility with cationic materials and stability of the formula. The anionic polymer may be a homopolymer or a copolymer. The present invention may select a polymer with amphoteric character, such that its oleophilic portions bind to the anti-dandruff active and its hydrophilic portions are available to interact with the added cationic polymer.

Anionic polymers useful herein include, for example, sodium polynaphthalene sulfonate, Sodium Lignosulfonate, sodium carboxymethyl cellulose, Sodium salt of hydrophobically modified maleic anhydride copolymer, Sodium polyacrylate, sodium polymethacrylate, ammonium polyacrylate, ammonium polymethacrylate, Sodium salt of polymethacrylic acid, sodium polynaphthalene sulfonate, and sodium carboxymethyl cellulose, and sodium polynaphthalene sulfonate, sodium polynaphthalene sulfonate having a tradename Darvanl Spray Dried, supplied from RT Vanderbilt having a molecular weight of about 3,000 g/mol in comparison to standards of sodium poly(styrenesulfonate) and a charge density of from about 3.5 to about 4.0 meq/g. Other suitable anionic polymers include hydrophobically modified crosslinked anionic polymers, such as acrylates/C10-30 alkyl acrylate crosspolymer, sold under the trade name Carbopol by Lubrizol or Aqupec by Presperse.

Cationic Polymer

The composition of the present invention comprises a high-charge-density cationic polymer, with a charge density of 3 to 10 meq/gram; from 4 to 8 meq/gram; from 5 to 7 meq/gram so as to bind strongly with the anionic polymer on the surface of the anti-dandruff active particle. The cationic polymer may be natural or synthetic, polymerized from a single monomer or synthesized as a copolymer. The cationic polymer may be polyquaternium-6, i.e., homopolymer of diallyldimethylammonium chloride, manufactured by Solvay under the trade name Mirapol 100, and by Lubrizol under the trade name Merquat 100, with a charge density of 6.2 meq/g. Other suitable cationic polymers include polyquaternium-2 (Solvay, trade name Mirapol A-15, 6.6 meq/g), polyquaternium-16 (BASF, trade name Luviquat FC-905, 6.1 meq/g), polyquaternium-17 (Solvay, trade name Mirapol AD-1, 4.4 meq/g), polyquaternium-22 (Lubrizol, trade names Merquat 280 (5.0 meq/g) and Merquat 295 (6.1 meq/g)), polyquaternium-42 (Buckman Labs, trade name Busan 1507, 7.8 meq/g) , and polyMAPTAC (polymer of Methacrylamidopropyltrimethylammonium chloride, Solvay, trade name Polycare 133, 4.5 meq/g).

The cationic polymer can be included in the composition at a level by weight of from about 0.001% to about 1%, from about 0.01% to about 0.5%, from about 0.02% to about 0.3% from about 0.05% to about 0.2%, in view of providing improved deposition of scalp actives.

In the present invention the cationic polymer and the anti-dandruff active may be included such that the weight ratio of cationic polymer to the anti-dandruff active is from about 1:2 to about 1:100 ; from about 1:5 to about 1:50; from about 1:10 to about 1:20 in view of providing improved active deposition while avoiding stickiness, hair clumping and/or build up.

The polyquaternium-6 useful herein may have a cationic charge density of from about 3.5meq/g; from about 4.5 meq/g; from about 5.5 meq/g in view of providing improved deposition of the active ingredient, and to about 13 meq/g; to about 10 meq/g; to about 7.0 meq/g, in view of achieving the desired particle size and appropriate coacervate adhesive properties to enhance active deposition.

The cationic polymer useful herein is that having a molecular weight of about 800 g/mol or more; of about 1,000 g/mol or more; of about 1,200 g/mol or more in view of providing improved active deposition. The molecular weight may also be to about 1,000,000 g/mol; to about 500,000 g/mol; to about 100,000 g/mol; to about 50,000 g/mol in view of providing better conditioning while providing improved active deposition Commercially available examples of polyquaternium-6 polymer include, for example, that having a tradename Merquat 100 available from Lubrizol, which has a cationic charge density of about 6.19 meq/g, molecular weight of about 150,000g/mol, and that having a tradename Merquat 106 available from Lubrizol, which has a cationic charge density of about 6.19 meq/g, molecular weight of about 15,000g/mol.

Soluble Cationic Polymer

The hair care composition may also comprise a low-charge-density polymer to achieve conditioning independent of active deposition. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-cross-linked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

In the present invention, the cationic polymer, may be, including but not limited, to a cationic guar polymer, has a weight average Molecular weight of less than 2.2 million g/mol, or from about 150 thousand to about 2.2 million g/mol, or from about 200 thousand to about 2.2 million g/mol, or from about 250 thousand to about 2.5 million g/mol, or from about 300 thousand to about 1.2 million g/mol, or from about 700,000 thousand to about 1 million g/mol. Further, the cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.8 meq/g.

The cationic guar polymer may have a weight average Molecular weight of less than about 1.5 million g/mol, and has a charge density of from about 0.1 meq/g to about 2.5 meq/g. The cationic guar polymer may have a weight average molecular weight of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The cationic guar polymer may be formed from quaternary ammonium compounds. The quaternary ammonium compounds for forming the cationic guar polymer may conform to the general formula 1:

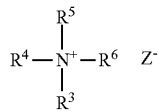

wherein where $R^3$, $R^4$ and $R^5$ are methyl or ethyl groups; $R^6$ is either an epoxyalkyl group of the general formula 2:

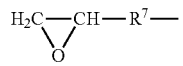

or $R^6$ is a halohydrin group of the general formula 3:

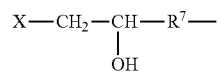

wherein $R^7$ is a $C_1$ to $C_3$ alkylene; X is chlorine or bromine, and Z is an anion such as Cl—, Br—, I— or $HSO_{4-}$.

The cationic guar polymer may conform to the general formula 4:

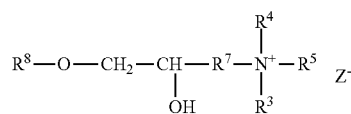

wherein $R^8$ is guar gum; and wherein $R^4$, $R^5$, $R^6$ and $R^7$ are as defined above; and wherein Z is a halogen. The cationic guar polymer may conform to Formula 5:

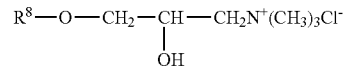

Suitable cationic guar polymers include cationic guar gum derivatives, such as guar hydroxypropyltrimonium chloride. The cationic guar polymer may be a guar hydroxypropyltrimonium chloride. Specific examples of guar hydroxypropyltrimonium chlorides include the Jaguar® series commercially available from Solvay, for example Jaguar® C-500, commercially available from Solvay. Jaguar® C-500 has a charge density of 0.8 meq/g and a molecular weight of 500,000 g/mol. Other suitable guar hydroxypropyltrimonium chloride are:

guar hydroxypropyltrimonium chloride which has a charge density of about 1.3 meq/g and a molecular weight of about 500,000 g/mol and is available from Solvay as Jaguar® Optima. Other suitable guar hydroxypropyltrimonium chloride are: guar hydroxypropyltrimonium chloride which has a charge density of about 0.7 meq/g and a molecular weight of about 1,500,000 g/mol and is available from Solvay as Jaguar® Excel. Other suitable guar hydroxypropyltrimonium chloride are: guar hydroxypropyltrimonium chloride which has a charge density of about 1.1 meq/g and a molecular weight of about 500,000 g/mol and is available from ASI, a charge density of about 1.5 meq/g and a molecular weight of about 500,000 g/mole is available from ASI.

Other suitable guar hydroxypropyltrimonium chloride are: Hi-Care 1000, which has a charge density of about 0.7 meq/g and a Molecular weight of about 600,000 g/mole and is available from Solvay; N-Hance 3269 and N-Hance 3270, which have a charge density of about 0.7 meq/g and a molecular weight of about 425,000 g/mol and are available from ASI; N-Hance 3196, which has a charge density of about 0.8 meq/g and a molecular weight of about 1,100,000 g/mol and is available from ASI. AquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.5 meq/g and M. Wt. of about 800,000 both available from ASI.

The hair care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units.

The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

The non-guar galactomannan polymer derivatives may have a M. Wt. from about 1,000 to about 10,000,000, and/or from about 5,000 to about 3,000,000.

The hair care compositions of the invention can also include galactomannan polymer derivatives which have a cationic charge density from about 0.5 meq/g to about 7 meq/g. The galactomannan polymer derivatives may have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

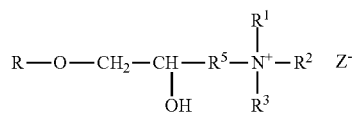

wherein R is the gum. The cationic galactomannan derivative can be a gum hydroxypropyltrimethylammonium chloride, which can be more specifically represented by the general formula 7:

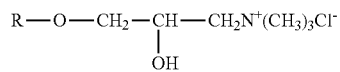

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 1,000 g/mol to about 10,000,000 g/mol, and/or from about 50,000 g/mol to about 1,000,000 g/mol, and/or from about 100,000 g/mol to about 900,000 g/mol, and/or from about 150,000 g/mol to about 400,000 g/mol and a cationic charge density from about 1 meq/g to about 5 meq/g, and/or from 2 meq/g to about 4 meq/g and can be derived from a cassia plant.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers disclosed herein have a percent of bound nitrogen of from about 0.5% to about 4%.

The cationically modified starch polymers for use in the hair care compositions can have a molecular weight about 850,000 g/mol to about 1,500,000 g/mol and/or from about 900,000 g/mol to about 1,500,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance of about 80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:
(i) an acrylamide monomer of the following Formula AM:

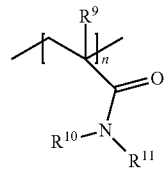

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and (ii) a cationic monomer conforming to Formula CM:

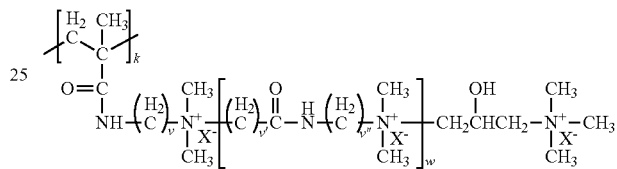

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

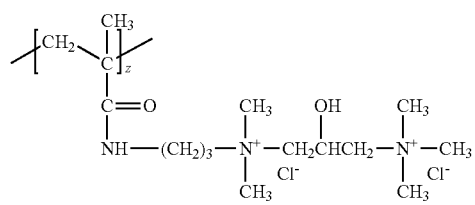

The above structure may be referred to as diquat. Alternatively, the cationic monomer can conform to Formula CM and wherein v and v" are each 3, v'=1, w=1, y=1 and $X^-$ is $Cl^-$, such as:

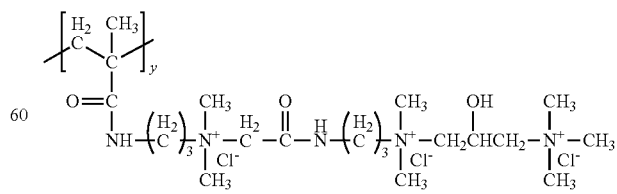

The above structure may be referred to as triquat.

Suitable acrylamide monomers include, but are not limited to, either acrylamide or methacryl amide.

The cationic copolymer (b) can be AM:TRIQUAT which is a copolymer of acrylamide and 1,3-Propanediaminium, N-[2-[[[dimethyl[3-[(2-methyl-1-oxo-2-propenyl)amino]propyl]ammonio]acetyl]amino]ethyl]2-hydroxy-N,N,N',N',N'-pentamethyl- , trichloride. AM:TRIQUAT is also known as polyquaternium 76 (PQ76). AM:TRIQUAT may have a charge density of 1.6 meq/g and a molecular weight of 1.1 million g/mol.

Further, the cationic copolymer may be of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. The cationized esters of the (meth)acrylic acid containing a quaternized N atom may be quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom may be dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with Cl to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 100 thousand g/mol to about 1.5 million g/mol, or from about 300 thousand g/mol to about 1.5 million g/mol, or from about 500 thousand g/mol to about 1.5 million g/mol, or from about 700 thousand g/mol to about 1.0 million g/mol, or from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC may have a charge density of about 1.3 meq/g and a molecular weight of about 1.1 million g/mol. The cationic copolymer can be AM:ATPAC. AM:ATPAC can have a charge density of about 1.8 meq/g and a molecular weight of about 1.1 million g/mol.

(a) Cationic Synthetic Polymers

The hair care composition can comprise a cationic synthetic polymer that may be formed from
i) one or more cationic monomer units, and optionally
ii) one or more monomer units bearing a negative charge, and/or
iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

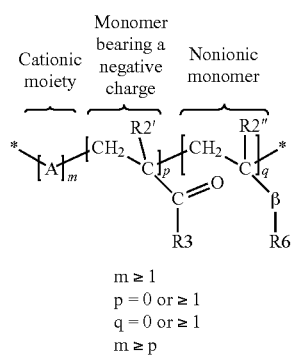

$m \geq 1$
$p = 0$ or $\geq 1$
$q = 0$ or $\geq 1$
$m \geq p$ where A, may be one or more of the following cationic moieties:

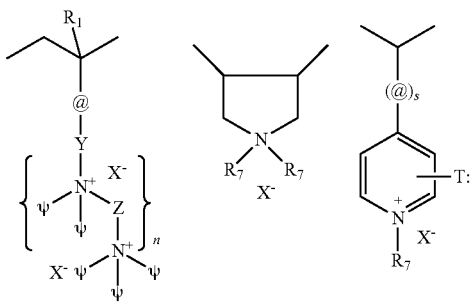

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;.
where Z=C1-C22 alkyl, alkyloxy, aryl or aryloxy;
where R1=H, C1-C4 linear or branched alkyl;
where s=0 or 1, n=0 or $\geq 1$;
where T and R7=C1-C22 alkyl; and
where X–=halogen, hydroxide, alkoxide, sulfate or alkylsulfate.

Where the monomer bearing a negative charge is defined by R2'=H, C1-C4 linear or branched alkyl and R3 as:

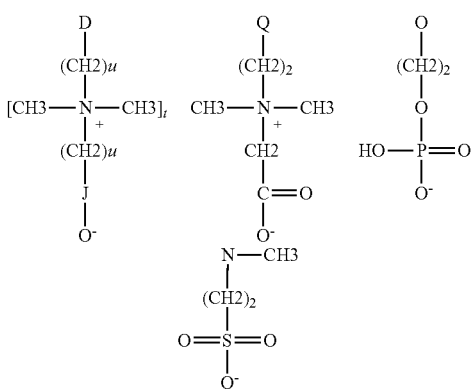

where D=O, N, or S;
where Q=NH$_2$ or O;
where u=1-6;
where t=0-1; and
where J=oxygenated functional group containing the following elements P, S, C.

Where the nonionic monomer is defined by R2″=H, C1-C4 linear or branched alkyl, R6=linear or branched alkyl, alkyl aryl, aryl oxy, alkyloxy, alkylaryl oxy and β is defined as

and
where G' and G″ are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula –NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X-) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The cationic polymer described herein can aid in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the hair care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable hair care composition that provides improved conditioning performance, with respect to damaged hair.

Cationic synthetic polymers that can form lyotropic liquid crystals may have a cationic charge density of from about 2 meq/gm to about 7 meq/gm, and/or from about 3 meq/gm to about 7 meq/gm, and/or from about 4 meq/gm to about 7 meq/gm. The cationic charge density may be about 6.2 meq/gm. The polymers also have a M. Wt. of from about 1,000 to about 5,000,000, and/or from about 10,000 to about 1,500,000, and/or from about 100,000 to about 1,500,000.

The cationic synthetic polymers that provide enhanced conditioning and deposition of benefit agents but do not necessarily form lyotropic liquid crystals may have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 1,500,000, from about 10,000 to about 1,500,000, and from about 100,000 to about 1,500,000.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Non-limiting examples include: JR-400, JR-125, JR-30M, KG-30M, JP, LR-400 and mixtures thereof. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Suitable cationic cellulose polymers may have a cationic charge density of from about 0.5 meq/gm to about 2.5 meq/gm, and/or from about 0.6 meq/gm to about 2.2 meq/gm, and/or from about 0.6 meq/gm to about 2.0 meq/gm. Further, the cationic charge density may be about 1.9meq/gm. The polymers also have a M. Wt. of from about 200,000 to about 3,000,000, and/or from about 300,000 to about 2,200,000, from about 1,000,000 to about 2,200,000 and/or from about 300,000 to about 1,500,000. The cationic cellulose polymer may have a cationic charge density of about 1.7 to about 2.1 meq/gm and a molecular weight of from about 1,000,000 to about 2,000,000.

The concentration of the cationic polymers ranges about 0.01% to about 5%, from about 0.08% to about 3%, from about 0.1% to about 2%, and/or from about 0.2% to about 1%, by weight of the hair care composition.

Aqueous Carrier

The personal care composition comprises an aqueous carrier. Accordingly, the formulations of the personal care composition can be in the form of pourable liquids (under ambient conditions). Such compositions will therefore typically comprise an aqueous carrier, which is present at a level of from about 20 wt. % to about 95 wt. %, or from about 60 wt. % to about 85 wt. %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the personal care composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, dipropylene glycol, hexylene glycol, glycerin, and propane diol.

Emulsifiers

In cases where the personal care composition does not include a gel matrix, an emulsifier may be used and materials may be pre-emulsified before added in the personal care composition.

Emulsifiers selection for each conditioning active is guided by the Hydrophilic-Lipophilic-Balance value (HLB value) of emulsifiers. Suitable range of HLB value is 6-16; an HLB value of 8-14. Emulsifiers with an HLB higher than 10 are water soluble. Emulsifiers with low HLB are lipid soluble. To obtain suitable HLB value, a mixture of two or more emulsifiers may be used. Suitable emulsifiers include non-ionic, cationic, anionic and amphoteric emulsifiers.

Rheology Modifier/Thickener

The personal care compositions mentioned above may also contain one or more rheology modifier/thickener to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. Further, the leave-on treatment may comprise from about 0.01% to about 3% of a rheology modifier, alternatively from about 0.1% to about 1% of a rheology modifier, The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG—(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/ isohexadecane/ polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14isoparaffin/laureth-7 ; poly acrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E 10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and/or combinations thereof.

A non exclusive list of suitable thickeners for use herein include xanthan, guar, hydroxypropyl guar, scleroglucan, methyl cellulose, ethyl cellulose (commercially available as Aquacote (Registered trademark), hydroxyethyl cellulose (Natrosol (Registered trademark), carboxymethyl cellulose, hydroxypropylmethyl cellulose, microcrystalline cellulose, hydroxybutylmethyl cellulose, hydroxypropyl cellulose (Klucel (Registered trademark), hydroxyethyl ethyl cellulose, cetyl hydroxyethyl cellulose (Natrosol (Registered trademark Plus 330), N-vinylpyrollidone (Povidone (Registered trademark), Acrylates/Ceteth-20 Itaconate Copolymer (Structure (Registered trademark 3001), hydroxypropyl starch phosphate (Structure (Registered trademark ZEA), polyethoxylated urethanes or polycarbamyl polyglycol ester (e.g. PEG-150/Decyl/SMDI copolymer =Aculyn (Registered trademark 44, PEG-150/Stearyl/SMDI copolymer=Aculyn 46 (Registered trademark), trihydroxystearin (Thixcin (Registered trademark) acrylates copolymer (e.g. Aculyn (Registered trademark 33) or hydrophobically modified acrylate copolymers (e.g. Acrylates/Steareth-20 Methacrylate Copolymer=Aculyn (Registered trademark 22), and fatty alcohols, such as cetyl and stearyl alcohol, and combinations thereof.

In the present invention, ethylene glycol monostearate (EGMS) and/or ethylene glycol distearate (EGDS) and/or polyethylene glycol monostearate (PGMS) and/or polyethyleneglycol distearate (PGDS) may be suspending waxes used in the composition. There are several commercial sources for these materials. For Example, PEG6000MS ® is available from Stepan, Empilan EGDS/A® is available from Albright & Wilson.

pH

The personal care compositions mentioned above may also comprise one or more pH adjusting material. The personal care compositions may have a pH in the range from about 2 to about 10, at 25° C. The personal care composition may have a pH in the range of from about 2 to about 6, alternatively from about 3.5 to about 5, alternatively from about 5.25 to about 7.

The personal care compositions mentioned above may further comprise one or more pH buffering agent. Suitable buffering agents are well known in the art and include for example ammonia/ammonium acetate mixture and monoethanolamine (MEA). The rinse-off conditioner composition may comprise citric acid, wherein the citric acid acts as a buffer.

Optional Ingredients

The personal care compositions described herein may optionally comprise one or more additional components known for use in personal care or personal care products, provided that the additional components are physically and chemically compatible with the essential components described herein, or do not otherwise unduly impair product stability, aesthetics or performance Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt. % to about 10 wt. % by weight of the personal care compositions.

Non-limiting examples of additional components for use in the personal care compositions include conditioning agents, natural cationic deposition polymers, synthetic cationic deposition polymers, other anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The personal care compositions may comprise one or more conditioning agents. Conditioning agents include materials that are used to give a particular conditioning benefit to hair. The conditioning agents useful in the personal care compositions of the present invention typically comprise a water-insoluble, water-dispersible, non-volatile, liquid that forms emulsified, liquid particles. Suitable conditioning agents for use in the personal care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt. % to about 10 wt. %, from about 0.1 wt. % to about 8 wt. %, and from about 0.2 wt. % to about 4 wt. %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

The personal care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as hair conditioners, and treatment products; and any other form that may be applied to hair. The personal care composition may be a hair mask, cowash, hair wax, hair clay, hair food, hair milk, hair pudding and hair gels.

The personal care compositions may include compositions applied to hair on scalp, hair on other areas of the body such as face including beards, under arms, torso, legs, or other areas of skin with hair and may include beard washes and shave preparations.

As is described below, the anti-dandruff active, anionic polymer and cationic polymer are combined prior to introduction to the personal care composition, which is generally prepared by conventional methods such as are known in the art of making personal care compositions. Such methods typically involve mixing of the ingredients in one or more steps to a relatively uniform state, with or without heating, cooling, application of vacuum, and the like. Aside from the pre-combination of active, anionic polymer, and cationic polymer, the sequence of ingredient additions can be varied for ease of processing and chemical compatibility. The compositions are prepared such as to optimize stability (physical stability, chemical stability, photostability) and/or delivery of the active materials.

Methods

Mixing of Active, Anionic Polymer and Cationic Polymer

The combination of the active with the anionic polymer can be performed in any suitable mixing vessel, such as a stirred tank, or an inline device such as a homogenizer, rotor-stator mill or static mixer. A suitable quantity of water or other liquid carriers can be included in this step e to reduce the viscosity of the composition to an acceptable level for ease of blending. To maximize deposition efficiency, the present invention may blend all of the active and the anionic polymer together prior to adding the cationic polymer. While completing, this coupling reaction step can include enough mixing intensity and solvent dilution to avoid formation of large agglomerates that are unsuitable for personal care compositions due to increased instability and consumer objections due to the presence of large agglomerates in personal care products.

The present invention may use a device for imparting enough mixing intensity at the point of introduction of the cationic polymer such a rotor-stator mill. Static mixers, homogenizers, sonolators and other high-energy devices are also suitable. Agitated tanks may deliver sufficient mixing intensity for low charge densities and significant dilution of the cationic polymer or the blend of the active and cationic polymer.

The desired ratios of active, anionic polymer, and cationic polymer can be controlled by combining them in a continuous process at suitable flow rates and concentrations of each ingredient to achieve the desired amount of each component in the final composition. For production at industrial scale, flow rates of 1 to 1000 kg per minute of each ingredient may be used, while laboratory quantities may be processed at lower flow rates, such as 0.001 to 1 kg per minute. The total mixing flow rate is computed by adding together the flow rates of the cationic polymer stream, the stream containing the anti-dandruff active and the anionic polymer. Although a continuous process is generally used, a batch process may also be contemplated, such as by introducing the cationic polymer to the other components in a recirculation line, or to an agitated tank with sufficient mixing intensity to avoid undesired large agglomerates.

The particulate active may be received from a supplier at an active concentration of 5% to 90% by weight, or from 10% to 70% by weight, or in a solid form requiring dilution in a liquid carrier prior to use. The slurry of particulate active may contain other processing aids, and the present invention demonstrates that the primary dispersant for the active may be the anionic polymer for the later coupling reaction to the cationic polymer, to maximize the adherence of the anionic polymer to the surface of the particulate active. The anionic polymer may be added by the supplier, in a pure or diluted form, as part of the active supplier's normal making process, or added later specifically for the personal care composition.

The cationic polymer can be dissolved in a liquid carrier, and optionally diluted, prior to use. Cationic polymers are often supplied as concentrated, viscous solutions that are difficult to process successfully in the present invention. Diluting with a suitable carrier, such as water, reduces the cationic polymer's viscosity and provides space between the polymer molecules, reducing the danger of excessive agglomeration.

It is generally desired to minimize the amount of water or other solvents used from the entire personal composition in the coupling reaction, for maximum formulation flexibility. However, if the components of the coupling reaction are too concentrated for the mixing intensity achievable in the selected mixing equipment, large agglomerates can occur. In general, higher mixing intensity allows for the materials to be more concentrated when combined, reducing the amount of liquid carrier needed to be reserved for the coupling reaction, thus widening the range of personal care compositions that can incorporate the invention. The present invention has found that active concentrations of from about 8% to 80% by weight, from about 5% to 65% by weight; from about 20% to 55% by weight, are most suitable for the composition comprising active, anionic polymer, and liquid carrier at the point of contact with the cationic polymer. The present invention has found that cationic polymer concentrations of from about 1% to 40%; from about 3% to 30%; from about 5% to 20%, provides a balance between minimizing the risk of undesirably large structures and reserving sufficient liquid for the manufacture of the full personal care composition.

Particle size is a consideration when selecting the process variables for the coupling reaction. The desired size of the final active complex may be from about 0.1 to 10 microns; from about 0.2 to 4 microns; when employing a low-charge-density cationic polymer as a deposition aid. Alternatively, a particle size of from about 12 to 100 microns; from about 20 to 50 microns, may be advantageous for deposition via a filtration mechanism. Particle sizes greater than 100 microns are generally not desirable, due to greater difficulty in suspending them in the final personal care composition and the potential for consumer rejection of the product.

The present invention recognizes that the charge density of the anionic and cationic polymers, the concentration of the ingredients, the mixing intensity, and the particle size of the native anti-dandruff active can all impact the particle size distribution of the complexed active and thus the particle performance in the final product. In general, small complexed particles are generated from small actives, low ingredient concentrations, low charge densities, and high mixing intensities. In addition, a higher ratio of active to total polymer (anionic+cationic), such as 5:1 by weight to 100:1 by weight, to maximize the bioavailability of the active upon deposition on the consumer's body. Lower ratios of active to total polymer, such as 1:1, are less desirable due to higher cost and potential reduction in bioavailability of the active.

The minimum mixing intensity and stream dilutions to avoid large particles can be determined in analysis. For example, a vessel containing the active and the anionic polymer (mixture a) at a total solids weight percent of 40%, or 25%, or 50%, can be connected to the inlet of a small pump. The outlet of the pump can be connected by piping to the inlet of an IKA Magic Lab rotor-stator mill equipped with three fine rotor-stator sets. A second vessel, containing the cationic polymer at a concentration of 10%, or 5%, or 12% can be connected to the inlet of a second pump. The outlet of the second pump can be piped to a second inlet port to the same IKA Magic Lab mill. The first pump can be set to a suitable flow rate, such as 0.2 kg/min, while the second pump is set to a reasonable flow rate, such as 0.02 kg/min, so as to achieve a flow ratio of about 10:1, or about 1:1 or about 50:1 for the first pump to the second pump of from about 10:1 to about 50:1. Material can be collected from the outlet of the mill at different mill speeds, such as 5000 revolutions per minute or 15000 revolutions per minute. By measuring the resulting particle size of the samples, the minimum mill speed can be determined that keeps the maximum particle size below a specified tolerance, such as 100 microns or 70 microns. If the achievable particle size is too large at the maximum attainable mill speed, the concentration of either feed stream can be reduced to improve results.

In the present invention, it may be useful to alter the choice of the cationic polymer or anionic polymer, such as by reducing the charge density, to improve results. The cohesive properties and degree of binding of the anionic-cationic polymer complex on the surface of the active particulate, and thus the effectiveness of the structure in depositing large quantities of bioavailable active, can be manipulated through ordinary changes in the chemistry of the system components.

Measurement of Maximum Agglomerate Size

The present invention may generate a narrow particle-size distribution or a fairly broad distribution. Particularly when the distribution is broad, the key measure of particle size is the maximum particle size, so as to avoid consumer complaints from visible particles and to avoid physical instability. Light microscopy on an ordinary microscopy equipped with Nomarski optics, such as a Zeiss Axioscop 2.0 may be used for determining this maximum particle size.

Approximately 10 microliters of the final personal care composition is transferred to a glass slide, then spread out underneath a glass coverslip. Ten 200 um by 200 um images at 40× magnification are taken at random from the prepared sample. The size of the largest particle in each of the ten images is determined using Zen Core software from the Zeiss corporation. The largest size found from these ten random images is reported as the maximum particle size. If an observed particle occupies more than half the image area, the maximum particle size is reported as ">100 um" and no further quantification is performed. For most applications, the method of making is deemed successful if no particles of 100 um or greater are found in the ten random 40× microscopy images.

In Vivo Scalp Deposition Testing

Scalp active deposition in-vivo on scalp can be determined by solvent extraction of the agent after the scalp has been treated with a scalp active containing composition either after application, after rinsing either immediately or at a delayed time point. An appropriate solvent for active extraction, such as ethanol or ethyl acetate or the like, can be selected for the active of interest based on solubility considerations, laboratory safety, and other practical considerations. The concentration of agent in the extraction solvent is measured by HPLC. Quantitation is made by reference to a standard curve. The concentration detected by HPLC is converted into an amount collected in grams by using the concentration multiplied by volume. The mass per volume concentration of the agent measured by HPLC is then converted to a mass per area amount deposited by multiplying the measured HPLC concentration by the volume of extraction solvent divided by the area of the scalp extracted.

In the present invention the particulate scalp active may provide a deposition of greater than about 1 ug/cm2; provides a deposition of greater than about 4 ug/cm2; provides a deposition greater than about 10 ug/cm2.

In the present invention "Mixing method" refers to the specific process of combining the stream containing the antimicrobial active with the stream containing the cationic polymer. In the present invention, "Mixing ratio" specifies the weight ratio of the active stream to the cationic polymer stream in the total composition. In the present invention, "Mixing flow rate" is the sum of the active stream flow rate and the cationic polymer stream flow rate, in grams per minute.

EXAMPLES AND COMPOSITIONS

The following examples illustrate non-limiting examples of the invention described herein. The exemplified personal care compositions can be prepared by conventional formulation and mixing techniques, and further in the combination of the cationic polymer with the active as described above. All parts, percentages, and ratios herein are by weight unless otherwise specified. Some components may come from suppliers as dilute solutions. The amount stated reflects the weight percent of the active material, unless otherwise specified.

The following examples further describe and demonstrate non-limiting examples within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Shampoo Examples

TABLE 1

COMPOSITION for BASE SHAMPOOS

| Material | Supplier | BASE A | BASE B |
| --- | --- | --- | --- |
| 29% sodium lauryl sulfate | BASF (trade name Texapon LS 30) | 5.2 | 23.5 |
| 25% sodium laureth sulfate | Stepan (trade name Steol CS-130) | 53.1 | 20.8 |
| 85% cocamide MEA | BASF | 1.2 | 1.2 |
| 30% cocamidopropyl betaine | Solvay (trade name Mackam C37 HP) | 3.3 | 3.3 |
| Zinc carbonate | Brueggemann | 1.61 | 0 |
| Ethylene glycol distearate | Evonik | 1.5 | 2.5 |
| Sodium benzoate | Emerald | 0.25 | 0.23 |
| Sodium salicylate | JQC Huayin Pharmaceutical | 0 | 0.15 |
| Methylchloroisothiazoline/methylisothiazoline | Dow (trade name Kathon CG) | 0.05 | 0 |
| 30% acrylates copolymer | Lubrizol (trade name Carbopol Aqua SF-1) | 0 | 1.67 |
| fragrance | Firmenich | 0.8 | 1.0 |
| 30% hydrochloric acid | Hydrite Chemical | 1 | 0 |
| Citric acid | Archer Daniels Midland | 0 | 0.30 |
| Sodium chloride | Morton Salt | 1 | 0.12 |
| Water | Crystal Springs | q.s. to 94 | q.s. to 94 |

TABLE 2

EXAMPLES: (percent by weight)

| INGREDIENT | Ex 1 | Ex 2 | Comparative Ex 3 | Ex 4 | Ex 5 | Ex 6 | Ex 7 | Ex 8 | Ex 9 |
| --- | --- | --- | --- | --- | --- | --- | --- | --- | --- |
| Zinc pyrithione (a) | 1 | 1 | 1 | | | | | | |
| Sulfur (b) | | | | 2 | 2 | 2 | 2 | 2 | 2 |
| Selenium Sulfide (c) | | | | | | | | | |
| Azoxystrobin (d) | | | | | | | | | |
| Polynapthalene sulfonate (e) | 0.01 | 0.01 | | 0.030 | 0.004 | 0.030 | 0.004 | | |
| Acrylates/C10-30 Alkyl Acrylate Crosspolymer (f) | | | | | | | | 0.02 | 0.02 |
| Polyquaternium-6 (g) | | | | | | | | | |

TABLE 2-continued

| EXAMPLES: (percent by weight) | | | | | | | | | |
|---|---|---|---|---|---|---|---|---|---|
| Polyquaternium-6 (h) | 0.1 | 0.1 | | 0.03 | 0.03 | 0.06 | 0.06 | 0.03 | 0.06 |
| Polyquaternium-22 (i) | | | | | | | | | |
| Polyquaternium-23 (j) | | | | | | | | | |
| PolyMAPTAC (k) | | | | | | | | | |
| Guar Hydroxypropyltrimonium chloride (l) | | 0.15 | 0.30 | | | | | | |
| Polyquaternium-76 (m) | | | 0.01 | | | | | | |
| Decyl glucoside (n) | | | | 0.1 | 0.1 | 0.1 | 0.1 | 0.1 | 0.1 |
| Xanthan gum (o) | | | | | | | | | |
| Shampoo Base A | 94 | 94 | 94 | | | | | | |
| Shampoo Base B | | | | 94 | 94 | 94 | 94 | 94 | 94 |
| Water | q.s. | q.s. | q.s. | q.s. | q.s. | q.s. | q.s. | q.s. | q.s. |
| Dimethicone (p) | 0.7 | 0.7 | 0.7 | | | | | | |
| ZPT deposition, ug/cm^2 per weight % cationic polymer | 13 | 4 | 3 | | | | | | |
| D99 particle size, um | 20 | 20 | 2 | 40 | 40 | 35 | 35 | | 50 |
| Physically stable | Yes | Yes | Yes | Yes | Yes | Yes | Yes | | Yes |

| INGREDIENT | Ex 10 | Ex 11 | Ex 12 | Ex 13 | Ex 14 | Ex 15 | Comparative Ex 16 |
|---|---|---|---|---|---|---|---|
| Zinc pyrithione (a) | | | | | | | |
| Sulfur (b) | 2 | 2 | 2 | 2 | | | 2 |
| Selenium Sulfide (c) | | | | | 1 | | |
| Azoxystrobin (d) | | | | | | 1 | |
| Polynapthalene sulfonate (e) | | 0.015 | 0.015 | 0.015 | 0.029 | 0.023 | 0 |
| Acrylates/C10-30 Alkyl Acrylate Crosspolymer (f) | | | | | | | |
| Polyquaternium-6 (g) | 0.029 | | | | | | |
| Polyquaternium-6 (h) | | | | | 0.09 | 0.03 | 0.03 |
| Polyquaternium-22 (i) | | 0.029 | | | | | |
| Polyquaternium-23 (j) | | | 0.058 | | | | |
| PolyMAPTAC (k) | | | | 0.058 | | | |
| Guar Hydroxypropyltrimonium chloride (l) | | | | | | | |
| Polyquaternium-76 (m) | | | | | | | |
| Decyl glucoside (n) | 0.1 | 0.1 | 0.1 | 0.1 | | | |
| Xanthan gum (o) | 0.005 | 0.005 | 0.005 | 0.005 | | | |
| Shampoo Base A | | | | | | | |
| Shampoo Base B | 94 | 94 | 94 | 94 | 94 | 94 | 94 |
| Water | q.s. | q.s. | q.s. | q.s. | q.s. | q.s. | q.s. |
| Dimethicone (p) | | | | | | | |
| ZPT deposition, ug/cm^2 per weight % cationic polymer | | | | | | | |
| D99 particle size, um | 55 | | | | 14 | 25 | 350 |
| Physically stable | Yes | | | | Yes | Yes | No |

(a) Lonza
(b) Solvay
(c) Omkar
(d) Jiangsu Agrochem
(e) Vanderbilt Minerals, trade name Darvan 1
(f) Lubrizol, trade name Carbopol Ultrez 21
(g) Lubrizol, trade name Merquat 100
(h) Solvay, trade name Mirapol 100
(i) Lubrizol, trade name Merquat 280
(j) Solvay, trade name Mirapol A-15
(k) Solvay, trade name Polycare 133
(l) Solvay, trade name Jaguar C-500 **this is low-charge-density, outside the scope of invention
(m) Amerchol, tradename AM: Triquat
(n) BASF, tradename Plantaren 2000
(o) CP Kelco, trade name Keltrol CG
(p) Momentive Performance Materials, 330 Pa-s polydimethylsiloxane Results

TABLE 3

PROCESSING EXAMPLES

| Process Example | Composition Example | Wt % active in active stream | Wt % cationic in polymer stream | Mixing method | Mixing ratio | Mixing flow rate, kg/min | Mixing success Yes/No |
|---|---|---|---|---|---|---|---|
| 17 | Ex 1 | 40% | 6% | IKA DR2000/4 mill | 1.5 | 4 | Yes |
| 18 | Ex 1 | 40% | 15% | IKA DR2000/4 mill | 1.5 | 4 | No |
| 19 | Ex 1 | 40% | 6% | Stirred 50 liter tank, 100 rpm | 1.5 | 4 | No |
| 20 | Ex 9 | 45% | 6% | IKA Magic Lab mill | 16 | 0.22 | Yes |
| 21 | Ex 7 | 50% | 12% | IKA Magic Lab mill | 4 | 0.25 | Yes |
| 22 | Ex 7 | 50% | 6% | IKA Magic Lab mill | 8 | 0.23 | Yes |
| 23 | Ex 10 | 52% | 6% | IKA Magic Lab mill | 8 | 0.23 | Yes |
| 24 | Ex 10 | 52% | 6% | Sulzer SMX static mixer | 8 | 0.23 | Yes |
| 25 | Ex 7 | 50% | 6% | Stirred 0.5 liter tank, 150 rpm | 8 | 0.23 | No |

"Mixing method" refers to the specific process of combining the stream containing the antimicrobial active with the stream containing the cationic polymer
"Mixing ratio" specifies the weight ratio of the active stream to the cationic polymer stream in the total composition
"Mixing flow rate" is the sum of the active stream flow rate and the cationic polymer stream flow rate, in kilograms per minute
A "mixing success" occurs when no particles >100 microns are apparent in the final shampoo when observed under a Zeiss Axioscope using Nomarski microscopy and a 40X objective

TABLE 4

| Example # | Composition | AD active | Anionic disp. | +polymer | Step 2 process | Final AD active Particle size | Deposition | Stable Yes/No |
|---|---|---|---|---|---|---|---|---|
| 26 | Ex 1 | 1% ZPT | Darvan 1 | 0.1% DADMAC (polyquat-6) | IKA mill | 2-50 um | 1.3 ug/cm^2 | Yes |
| 27 | Ex 1 | 1% ZPT | Darvan 1 | 0.1% DADMAC | n/a (no step 2) | 2 um | 0.4 ug/cm^2 | Yes |
| 28 | Ex 2 (unstable) | 1% ZPT | Darvan 1 | 0.1% DADMAC | Impeller | 200 um | No data | No |
| 29 | Comparative Example 3 | 1% ZPT | Darvan 1 | 0.3% guar (low charge density) | n/a | 2 um | 1.1 ug/cm^2 | Yes |

TABLE 5

MEASURED PARTICLE SIZE OF SELECTED EXAMPLES

| Process Example | Composition Example | Wt % active in active stream | Wt % cationic in polymer stream | Mixing method | Mixing ratio | Mixing flow rate, kg/min | Particle size |
|---|---|---|---|---|---|---|---|
| 30 | Ex 10 | 52% | 6% | IKA Magic Lab mill | 8 | 0.27 | 64 um |
| 31 | Ex 10 | 52% | 6% | IKA Magic Lab mill | 4 | 0.30 | 66 um |
| 32 | Ex 11 | 52% | 6% | IKA Magic Lab mill | 8 | 0.27 | 75 um |
| 33 | Ex 11 | 52% | 6% | IKA Magic Lab mill | 4 | 0.30 | 80 um |
| 34 | Ex 12 | 52% | 6% | IKA Magic Lab mill | 8 | 0.27 | 64 um |
| 35 | Ex 12 | 52% | 6% | IKA Magic Lab mill | 4 | 0.30 | 80 um |

TABLE 5-continued

MEASURED PARTICLE SIZE OF SELECTED EXAMPLES

| Process Example | Composition Example | Wt % active in active stream | Wt % cationic in polymer stream | Mixing method | Mixing ratio | Mixing flow rate, kg/min | Particle size |
|---|---|---|---|---|---|---|---|
| 36 | Ex 13 | 52% | 6% | IKA Magic Lab mill | 8 | 0.27 | 90 um |
| 37 | Ex 13 | 52% | 6% | IKA Magic Lab mill | 4 | 0.30 | 80 um |
| 38 | Ex 11 | 52% | 6% | Sulzer SMX static mixer | 8 | 0.27 | 68 um |

Discussion

The examples in Table 3 provide further knowledge of our invention. Comparing Examples 17 and 18, it can be seen that a lower concentration of cationic polymer in the coupling reaction can help avoid the formation of undesirable large agglomerates. Comparing Examples 17 and 19, it can be seen that the higher mixing intensity of a rotor-stator mill relative to an impeller also helps eliminate excessively large particles on a larger scale. A comparison of Examples 23 and 25 provides a similar conclusion using smaller scale equipment. Example 24 illustrates that other high-shear equipment, such as static mixers, may be effectively substituted for a rotor-stator mill. Examples 20 and 21 illustrate that success can be achieved across a range of flow rates and polymer concentrations when using appropriately selected high mixing intensity equipment.

The examples in Table 4 illustrate the benefit of the invention as a deposition technology. The execution of precombining the active, anionic polymer and cationic polymer prior to introduction into the personal care composition (Example 26) shows more than a threefold deposition efficiency relative to the customary process of adding the cationic polymer separately to the personal care composition (Example 27). Example 28's undesired formation of large agglomerates is shown to be the direct result of the use of ordinary, low-shear impeller to combine ingredients, rather than the Example 26 process comprising high intensity mixing of the cationic polymer to the active plus anionic polymer. A comparison of Example 26's execution to Example 29's conventional formulation with low-charge-density polymer indicates an equal or greater total deposition of the active at one-third the total polymer level; e.g. 3× the effectiveness of the deposition aid.

Additional Examples/Combinations

Paragraph A A method of making a personal care composition comprising the following steps:
a) combine a particulate scalp active with an anionic polymer to form a mixture (a);
b) combine the mixture (a) with a cationic polymer having a charge density of 3 to 10 meq/gram to form a mixture (b);
c) combine mixture (b) into a personal care composition base.

Paragraph B A method of making a personal care composition according to Paragraph A wherein the cationic polymer is selected from the group consisting of polyquaternium-6, homopolymer of diallyldimethylammonium chloride, polyquaternium-2, polyquaternium-16, polyquaternium-17, polyquaternium-22, polyquaternium-42, poly-MAPTAC, polymer of Methacrylamidopropyltrimethylammonium chloride and mixtures thereof.

Paragraph C A method of making a personal care composition according to Paragraph A-B wherein the particulate scalp active is selected from the group consisting of zinc pyrithione, sulfur, selenium sulfide, azoxystrobin and mixtures thereof.

Paragraph D A method of making a personal care composition according to Paragraph A-C wherein there is a flow ratio of mixture (a) to the cationic polymer in step b is from about 1:1 to about 50:1.

Paragraph E A method of making a personal care composition according to Paragraph A-D wherein a ratio of the anionic polymer to particulate scalp active is from about 1:1 to about 1:100.

Paragraph F A method of making a personal care composition according to Paragraph A-E wherein a ratio of the anionic polymer to particulate scalp active is from about 1:5 to about 1:50.

Paragraph G A method of making a personal care composition according to Paragraph A-F wherein a ratio of the anionic polymer to cationic polymer is from about 1000:1 to about 1:35.

Paragraph H A method of making a personal care composition according to Paragraph A-G wherein the particulate scalp active is present at a level of about 0.25% to about 4% in the personal care composition.

Paragraph I A method of making a personal care composition according to Paragraph A-H wherein a ratio of the anionic polymer to cationic polymer is from about 10:1 to about 1:10.

Paragraph J A method of making a personal care composition according to Paragraph A-I wherein the particulate scalp active provides a deposition of greater than about 1 ug/cm2.

Paragraph K A method of making a personal care composition according to Paragraph A-J wherein particle size of the particulate scalp active is less than to 100 microns.

Paragraph L A method of making a personal care composition according to Paragraph A-K wherein the personal care composition is a shampoo.

Paragraph M A method of making a personal care composition according to Paragraph A-L wherein the personal care composition comprises a surfactant.

Paragraph N A method of making a personal care composition according to Paragraph A-M wherein the personal care composition comprises an anionic, amphoteric, nonionic or zwitterionic surfactant or mixtures thereof.

Paragraph O A method of making a personal care composition according to Paragraph A-N wherein the personal care composition further comprises a conditioning agent.

Paragraph P A method of making a personal care composition according to Paragraph A-O wherein the conditioning agent is a silicone.

Paragraph Q A method of making a personal care composition according to Paragraph A-P further comprising from about 0.5% to about 7% of a perfume.

Paragraph R A method of making a personal care composition according to Paragraph A-Q wherein a rotor stator mill is used in Step b.

Paragraph S A method of making a personal care composition according to Paragraph A-R wherein a ratio of particulate scalp active to a total polymer ratio of anionic polymer in combination with cationic polymer is from about 5:1 to about 100:1.

All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the personal care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular descriptions of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a personal care composition comprising the following steps:
   a) combine a particulate scalp active with an anionic polymer to form a mixture (a);
   b) combine the mixture (a) with a cationic polymer having a charge density of 3 to 10 meq/gram to form a mixture (b);
   c) combine mixture (b) into a personal care composition base;
   wherein there is a flow ratio of mixture (a) to the cationic polymer in step b is from about 1:1 to about 50:1.

2. A method of making a personal care composition according to claim 1 wherein the anionic polymer is selected from the group consisting of sodium polynaphthalene sulfonate, sodium lignosulfonate, sodium carboxymethyl cellulose, sodium salt of hydrophobically modified maleic anhydride copolymer, sodium polyacrylate, sodium polymethacrylate, ammonium polyacrylate, ammonium polymethacrylate, sodium salt of polymethacrylic acid, sodium polynaphthalene sulfonate, sodium carboxymethyl cellulose, sodium polynaphthalene sulfonate, sodium polynaphthalene sulfonate, hydrophobically modified cross-linked anionic polymers, acrylates/C10-30 alkyl acrylate crosspolymer, and mixtures thereof.

3. A method of making a personal care composition according to claim 1 wherein the cationic polymer is selected from the group consisting of polyquaternium-6, homopolymer of diallyldimethylammonium chloride, polyquaternium-2, polyquaternium-16, polyquaternium-17, polyquaternium-22, polyquaternium-42, polyMAPTAC, polymer of Methacrylamidopropyltrimethylammonium chloride and mixtures thereof.

4. A method of making a personal care composition according to claim 1 wherein the particulate scalp active is selected from the group consisting of zinc pyrithione, sulfur, selenium sulfide, azoxystrobin and mixtures thereof.

5. A method of making a personal care composition according to claim 1 wherein a ratio of the anionic polymer to particulate scalp active is from about 1:1 to about 1:100.

6. A method of making a personal care composition according to claim 1 wherein a ratio of the anionic polymer to particulate scalp active is from about 1:5 to about 1:50.

7. A method of making a personal care composition according to claim 1 wherein a ratio of the anionic polymer to cationic polymer is from about 1000:1 to about 1:35.

8. A method of making a personal care composition according to claim 1 wherein the particulate scalp active is present at a level of about 0.25% to about 4% in the personal care composition.

9. A method of making a personal care composition according to claim 1 wherein a ratio of the anionic polymer to cationic polymer is from about 10:1 to about 1:10.

10. A method of making a personal care composition according to claim 1 wherein the particulate scalp active provides a deposition of greater than about 1 ug/cm2.

11. A method of making a personal care composition according to claim 1 wherein particle size of the particulate scalp active is less than to 100 microns.

12. A method of making a personal care composition according to claim 1 wherein the personal care composition is a shampoo.

13. A method of making a personal care composition according to claim 1 wherein the personal care composition comprises a surfactant.

14. A method of making a personal care composition according to claim 1 wherein the personal care composition comprises an anionic, amphoteric, nonionic or zwitterionic surfactant or mixtures thereof.

15. A method of making a personal care composition according to claim 1 wherein the personal care composition further comprises a conditioning agent.

16. A method of making a personal care composition according to claim 15 wherein the conditioning agent is a silicone.

17. A method of making a personal care composition according to claim 1 further comprising from about 0.5% to about 7% of a perfume.

18. A method of making a personal care composition according to claim 1 wherein a rotor stator mill is used in Step b.

19. A method of making a personal care composition according to claim 1 wherein a ratio of particulate scalp active to a total polymer ratio of anionic polymer in combination with cationic polymer is from about 5:1 to about 100:1.

\* \* \* \* \*